(12) United States Patent
Rokni et al.

(10) Patent No.: US 8,336,391 B2
(45) Date of Patent: Dec. 25, 2012

(54) METHOD AND SYSTEM FOR NON-INVASIVELY MONITORING FLUID FLOW IN A SUBJECT

(75) Inventors: Michal Rokni, Zichron Ya'akov (IL);
Revital Pery Shechter, Rishon Lezion (IL); Ilan Breskin, Tel-Aviv (IL);
Michal Balberg, Jerusalem (IL);
Yaakov Metzger, Hod Hasharon (IL)

(73) Assignee: OR-NIM Medical Ltd., Lod (IL)

( * ) Notice: Subject to any disclaimer, the term of this patent is extended or adjusted under 35 U.S.C. 154(b) by 703 days.

(21) Appl. No.: 12/498,045

(22) Filed: Jul. 6, 2009

(65) Prior Publication Data

US 2010/0000330 A1 Jan. 7, 2010

Related U.S. Application Data

(60) Provisional application No. 61/078,410, filed on Jul. 6, 2008.

(51) Int. Cl.
*G01F 1/712* (2006.01)
(52) U.S. Cl. ..................................... 73/861.06
(58) Field of Classification Search .............. 73/861.06, 73/570.5; 356/436
See application file for complete search history.

(56) References Cited

U.S. PATENT DOCUMENTS

| | | | |
|---|---|---|---|
| 3,435,228 A | 3/1969 | Eugene | |
| 4,059,010 A | 11/1977 | Sachs | |
| 4,109,647 A | 8/1978 | Stern et al. | |
| 5,152,293 A | 10/1992 | Vonesh et al. | |
| 5,299,570 A | 4/1994 | Hatschek | |
| 5,579,774 A | 12/1996 | Miller et al. | |
| 6,002,958 A | 12/1999 | Godik | |
| 6,041,248 A | 3/2000 | Wang | |
| 6,047,602 A | 4/2000 | Lynnworth | |
| 6,216,538 B1 * | 4/2001 | Yasuda et al. | 73/570.5 |

(Continued)

FOREIGN PATENT DOCUMENTS

DE 196 54 053 A1 6/1998
(Continued)

OTHER PUBLICATIONS

Prahl, "Optical Absorption of Hemoglobin," OMLC, SAP (Jun. 1998) http://omlc.ogi.edu/spectra/hemoglobin/.

(Continued)

*Primary Examiner* — Jewel V Thompson
(74) *Attorney, Agent, or Firm* — Oliff & Berridge, PLC

(57) ABSTRACT

A monitoring system is presented for monitoring fluid flow in turbid medium. The fluid flow monitoring system comprises a processor utility which is connectable to an acoustic generator associated with one or more acoustic ports and is operable for generating signals $S_0$ to activate said one or more acoustic ports for irradiating a region of interest with acoustic radiation of a certain frequency range centered at a frequency $F_0$ and is connectable to at least one light output port associated with one or more light detectors for receiving light of at least one wavelength $\lambda$ from the region of interest including light tagged by said acoustic radiation. In some embodiments, the processor utility is configured and operable for analyzing the generated signals $S_0$ and data indicative of the received light including light tagged by the corresponding acoustic radiation and determining correlation between said signals $S_0$ and said data indicative of the received light, said correlation being informative of a measure of fluid flow in the medium.

23 Claims, 7 Drawing Sheets

U.S. PATENT DOCUMENTS

| | | |
|---|---|---|
| 6,456,862 B2 | 9/2002 | Benni |
| 6,498,942 B1 | 12/2002 | Esenaliev et al. |
| 6,590,830 B1 | 7/2003 | Garlick et al. |
| 6,615,065 B1 | 9/2003 | Barrett et al. |
| 6,690,958 B1 | 2/2004 | Walker et al. |
| 6,738,653 B1 | 5/2004 | Sfez et al. |
| 6,802,812 B1 | 10/2004 | Walker et al. |
| 6,815,694 B2 | 11/2004 | Sfez et al. |
| 6,957,096 B2 | 10/2005 | Sfez et al. |
| 7,049,622 B1 | 5/2006 | Weiss |
| 7,251,518 B2 | 7/2007 | Herrmann |
| 7,340,957 B2 * | 3/2008 | Kaduchak et al. ........... 73/570.5 |
| 7,541,602 B2 | 6/2009 | Metzger et al. |
| 7,747,301 B2 | 6/2010 | Cheng et al. |
| 2002/0017141 A1 | 2/2002 | Satoh |
| 2004/0127782 A1 | 7/2004 | Sfez et al. |
| 2005/0038344 A1 | 2/2005 | Chance |
| 2006/0247506 A1 | 11/2006 | Balberg et al. |
| 2008/0200787 A1 | 8/2008 | Shapira et al. |
| 2008/0296514 A1 | 12/2008 | Metzger et al. |

FOREIGN PATENT DOCUMENTS

| | | |
|---|---|---|
| WO | WO 2005/025399 A2 | 3/2005 |
| WO | WO 2006/097910 A1 | 9/2006 |
| WO | WO 2008/039195 A1 | 4/2008 |

OTHER PUBLICATIONS

Hueber et al., "Non-invasive and Quantitative Near-infrared Haemoglobin Spectrometry in the Piglet Brain during Hypoxic Stress, using a Frequency-domain Multidistance Instrument," 46 Phys. Med. Biol. 41-62 (2001).

Raichle et al., "Brain Work and Brain Imaging," 29 Anne. Rev. Neurosci. 449-476 (2006).

Takatani et al., "Theoretical Analysis of Diffuse Reflectance from a Two-layer Tissue Model," BME-26 IEEE Transactions on Biomedical Engineering 12 (Dec. 1979).

International Search Report issued on Nov. 6, 2009 in International Patent Application No. PCT/IL2009/000675.

* cited by examiner

METHOD AND SYSTEM FOR NON-INVASIVELY MONITORING FLUID FLOW IN A SUBJECT

This nonprovisional application claims the benefit of U.S. Provisional Application No. 61/078,410, filed Jul. 6, 2008. The disclosure of the prior application is hereby incorporated by reference in its entirety.

FIELD OF THE INVENTION

The invention is generally in the field of fluid flow measurements, and relates to a method and system for monitoring fluid flow through turbid media. The invention is particularly useful for medical applications such as measuring blood flow in a subject, as well as measurement of some other blood related parameters.

BACKGROUND OF THE INVENTION

Remote monitoring of fluid flow provides utility across a wide range of industrial and healthcare applications. In medical diagnosis, treatment and monitoring, there is frequent need to measure blood flow in order to monitor tissue perfusion, metabolism and general health. This need stems from the biological requirement for transport of oxygen and nutrients to tissues and the removal of waste products (M. E. Raichle and M. A. Mintun, "Brain work and brain imaging", Annu Rev Neurosci 2006; 29:449-476).

Existing methods for measuring biological flow include laser Doppler measures of reflected energy changes (as disclosed for example in U.S. Pat. No. 41,096,47), variation in impedance on the scalp surface (e.g. US 2008/0200787), or the use of invasive flowmeters implanted directly into the tissue (e.g. U.S. Pat. No. 5,579,774).

Various techniques for non-invasive measurements of blood related parameters have been developed. Such techniques include frequency-domain spectroscopy, and photoacoustic spectroscopy [D M Hueber et al Phys. Med. Biol. 46 (2001) 41-62].

A productive approach to non-invasive monitoring in healthcare settings is the use of ultrasound tagged light. (U.S. Pat. No. 7,541,602, WO 06/097910, WO 05/025399, all assigned to the assignee of the present application). In this method, the intersection of electromagnetic and acoustic signals has been used to monitor tissue optical properties.

GENERAL DESCRIPTION

There is a need in the art for a novel technique enabling the fluid flow measurement, such as blood flow, in a non-invasive, non-ionizing manner to limit discomfort and possible hazards to a patient.

The present invention utilizes the principles of ultrasound tagging of light to monitor flow within a turbid medium. More specifically, the tagging of light by acoustic radiation is used to determine the optical response of a region of interest in the medium, enabling determination of the flow within the region of interest from said optical response. More specifically, according to this technique, a region of interest in a subject (e.g. human body) is illuminated with light of at least one wavelength, and is irradiated with acoustic radiation (preferably ultrasound) such that the acoustic radiation overlaps the illuminated region in at least a part of the region of interest (this overlapping volume is termed "tagged volume"). Light scattered from the subject's body, including photons that are tagged by the acoustic radiation and those that are not, is appropriately detected.

The main idea of the invention is to extract information about the blood flow in a subject (generally fluid flow in turbid media) from acousto-optic measurements based on the ultrasound tagging of light. The inventors have found that correlation between light tagged by acoustic radiation and the signal which generates the corresponding acoustic radiation is indicative of a measure of fluid flow in the medium. Also, the inventors have found that a measure of blood flow can be obtained from data indicative of a power spectrum of the received light, including light tagged by the acoustic radiation, namely from the parameters of at least one peak in said power spectrum.

The following examples can be used to determine parameters of the signal that correspond to measures of flow. According to one not limiting example, for the case of blood flow in tissue, a measure of flow can be defined as: blood flow velocity (measured in cm/sec), blood perfusion (measured in mL (blood)/100 mg (tissue)/min), hemoglobin concentration ($G_{tot}$) as a function of time, oxygenated hemoglobin or oxygen saturation as a function of time.

According to one broad aspect of the invention, there is provided a monitoring system for monitoring fluid flow in a turbid medium. The system comprises a processor utility which is connectable to an acoustic generator associated with one or more acoustic ports and is operable for generating signals $S_0$ to activate said one or more acoustic ports for generating acoustic radiation of a certain frequency range centered at a frequency $F_0$ to irradiate a region of interest, and is connectable to at least one light output port associated with one or more light detectors for receiving light of at least one wavelength $\lambda$ from the region of interest including light tagged by said acoustic radiation. The processor utility is configured and operable for analyzing the generated signals $S_0$ and data indicative of the received light including light tagged by the corresponding acoustic radiation and determining correlation between said signals $S_0$ and said data indicative of the received light, said correlation being informative of a measure of fluid flow in the medium.

The acoustic signal has one of the following profiles: a continuous wave (CW); a modulated continuous wave (e.g. coded signal, e.g. coded signal with narrow autocorrelation); and/or a pulse or sequence of pulses.

In some embodiments of the invention, the processor utility is configured and operable to determine said correlation by carrying out the following:

determining cross correlation, $CCA(\tau, \lambda, T)$, between said signals $S_0$ and said data indicative of the received light, said cross correlation being calculated for each wavelength $\lambda$ of light and at a time delay $\tau$ from onset of the acoustic signal, and determining autocorrelation UTLA of said cross correlation $CCA(\tau, \lambda, T)$ at different times T, being time stamps of different measurement times, said autocorrelation UTLA being indicative of a measure of fluid flow within the medium as a function of depth z in the medium.

The autocorrelation UTLA for a predetermined $\tau$; being a function of $\Delta T$, $\tau$ and $\lambda$, can be determined as follows:

$$UTLA(\Delta T, \tau, \lambda) = \int dT \cdot CCA(T, \tau, \lambda) \cdot CCA(T + \Delta T, \tau, \lambda).$$

A measure of flow can be determined from a decay coefficient of $UTLA(\Delta T, \tau, \lambda)$.

The processor utility may be configured for measuring a decay time $T_{decay}$, thus providing information indicative of the measure of flow within the monitored medium. For example, the processor utility calculates the decay time $T_{decay}$ from a single UTLA signal or from a sum/average over such signals.

The monitoring system preferably includes a control panel associated with a measurement unit. This control panel includes said at least one light output, said one or more acoustic ports, and also at least one light input for illumination of the region of interest with light of one or more wavelengths. The light input(s) is/are associated with one or more light sources (e.g. lasers) producing light of different wavelengths, or with at least one tunable light source.

According to another broad aspect of the invention, there is provided a monitoring system for monitoring fluid flow in a turbid medium, the system comprising: a processor utility which is connectable to an acoustic generator associated with one or more acoustic ports and is operable for generating signals ($S_0$) to activate said one or more acoustic ports for irradiating a region of interest with acoustic radiation of a certain frequency range centered at a frequency $F_0$ and is connectable to at least one light output port associated with one or more light detectors for receiving light of at least one wavelength $\lambda$ from the region of interest including light tagged by said acoustic radiation, the processor utility being configured and operable for analyzing data indicative of a power spectrum of the received light including light tagged by the acoustic radiation; identifying in said data at least one of the following light intensity peaks: a peak around said frequency $F_0$, a peak around a harmonic of said frequency $F_0$; and determining a measure of the fluid flow according to parameters of said at least one peak.

In some embodiments, the processor utility may also analyze the data indicative of the received light to identify in said data a DC intensity peak and use the parameters of such at least two peaks for the fluid flow measure. The acoustic signal in this case may be in the form of a continuous wave or modulated continuous wave.

According to yet another broad aspect of the invention, there is provided, a control unit for use in monitoring fluid flow in a turbid medium. The control unit comprises a processor utility configured for communication with an acoustic generator for receiving data indicative of generated signals $S_0$ corresponding to signals which activate one or more acoustic ports for irradiating a region of interest with acoustic radiation of a certain frequency range centered at a frequency $F_0$, and for communication with one or more light detectors (or associated therewith one or more light output ports) for receiving data indicative of detected light of at least one wavelength $\lambda$ including light tagged by said acoustic radiation. The processor utility is configured for processing and analyzing data indicative of the detected light and generating output data indicative of correlation between said signals $S_0$ and said data indicative of the received light, said correlation being informative of a measure of the fluid flow in the medium.

More specifically, the invention is useful for blood flow measurements and is therefore described below with respect to this specific application.

BRIEF DESCRIPTION OF THE DRAWINGS

In order to understand the invention and to see how it may be carried out in practice, embodiments will now be described, by way of non-limiting examples only, with reference to the accompanying drawings, in which.

DETAILED DESCRIPTION OF EMBODIMENTS

Figure 1:
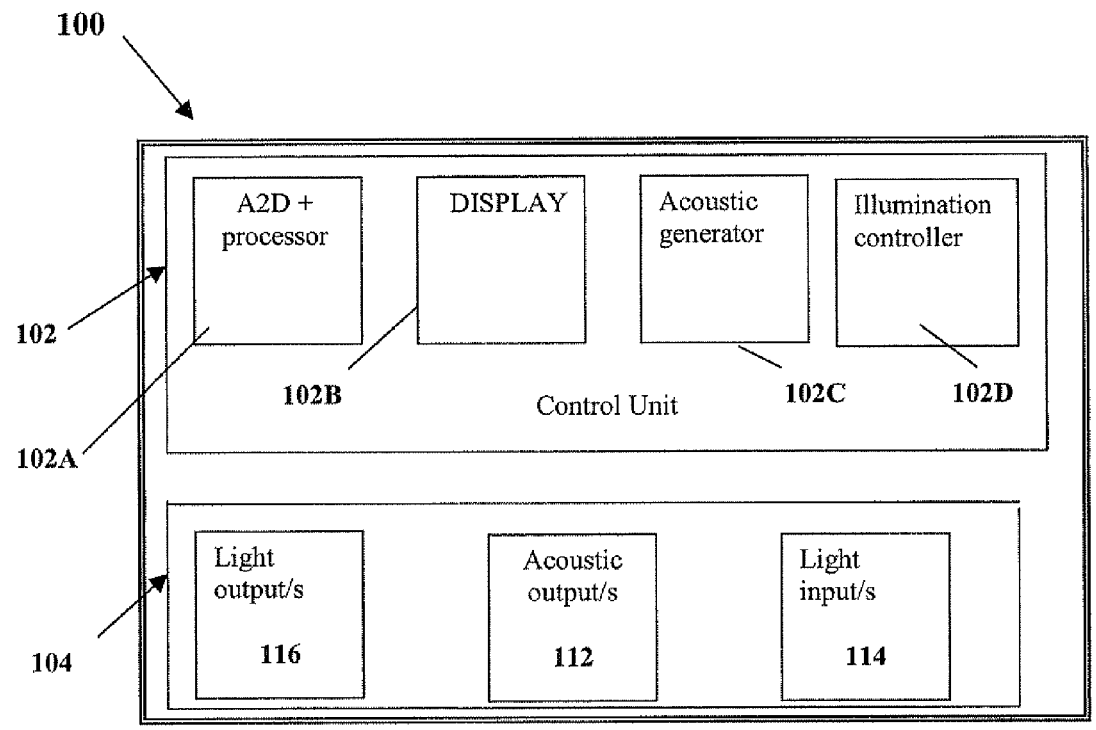
FIG. 1 is a block diagram of an example of a monitoring system of the present invention suitable for non-invasively measuring blood flow in a subject.

Reference is made to FIG. 1 showing schematically an example of a monitoring system, generally designated 100' configured and operable according to the invention for non-invasive monitoring of one or more blood related parameters including a blood flow parameter. System 100 is configured as a control station and includes a control unit 102 and a control panel 104 which is associated with a measurement unit. Control panel 104 is in communication with utilities of control unit 102 and with those of the measurement unit. At least a part of the control panel 104 may be integral with control unit 102 and configured to connect respective ports of the control panel to those of the to external measurement unit, or may be part of the measurement unit and connected to the control unit via wires or via wireless signal transmission.

Control panel 104 includes one or more light output ports 116, one or more light input ports 114, and one or more acoustic ports 112. Light output port(s) 116 is/are associated with one or more photodetectors either directly or via guiding element(s), e.g. optical fiber(s). Light input port(s) 114 is/are associated with one or more light sources (lasers) either directly or via guiding element(s), e.g. optical fiber(s). Control unit 102 includes inter alia a data processing utility 102A (including also an analog-to-digital converter), an acoustic generator 102C and a data presentation utility 102B such as display, as well as user interface (not shown). Also preferably provided in the control unit 102 is an illumination controller 102D. Illumination controller 102I) may be used for selecting one or more light inputs and/or one or more light outputs for the illumination and light collection from multiple ports.

Data processing utility 102A includes appropriate hardware and/or software modules. As will be described more specifically further below, the data processing utility includes inter alia a module capable of processing measured optical data coming from photodetector(s) (light output(s) 116) and signal $S_0$ from acoustic generator 102C and determining cross correlation, (CCA($\lambda$,$\tau$)), between signal $S_0$ indicative of acoustic (ultrasound) radiation (e.g. coded signal or continuous signal) and the corresponding measured data indicative of detected light including ultrasound tagged light signals. The data indicative of the detected light may be the amplitude of such signal or its absolute value, or another function corresponding to this signal. The output of such cross-correlator module includes for example amplitude or phase of the cross correlation at different delays of the acoustic signal, as will be described below.

Light input port(s) 114 is/are operated (e.g. via illumination controller 102D or manually by user) to deliver coherent laser light into the media (including a region of interest), and light scattered back from the tissue within the illuminated region (including at least a part of the region of interest) is collected by at least one light output port 116 that is associated with (coupled to) a photodetector. Acoustic generator 102C generates signals $S_0$ of certain frequency range, centered at frequency ($F_0$) and operates an ultrasound transducer (constituted by acoustic port 112) to emit ultrasound waves of said frequency ($F_0$) into the monitored medium that is simultaneously illuminated by the laser light, and when interacting with light in the media "tag" the light that travels through the medium. Therefore, some of the light detected at the light output 116 is modulated at the ultrasound frequency ($F_0$), or at the vicinity of the ultrasound frequency.

The generation of acoustic waves can be in one of the following modes: a continuous wave (CW), a modulated continuous wave (coded), or a single pulse or sequence of pulses (burst).

In some embodiments of the invention, the ultrasound is generated by a coded signal with a narrow autocorrelation. The principles of this technique are described in U.S. Pat. No. 7,541,602, assigned to the assignee of the present application and incorporated herein by reference with respect to this specific but not limiting example. The acoustic radiation generated into the turbid medium has a pressure profile $PA(\tau)$ within the medium; here $\tau$ is the time delay within a single ultrasound tagged signal $CCA(\lambda,\tau)$ from the onset of the acoustic wave. The "narrow autocorrelation function" refers to an autocorrelation which is negligible for any delay time $\tau$ larger than the determined time resolution of the system. The latter may for example be determined as the time resolution of detection of the electromagnetic radiation response, or as the temporal bandwidth of the acoustic excitation of the ultrasound transducer, or as the required spatial resolution divided by the speed of sound in the media.

Light of wavelength $\lambda$ is irradiated into the medium (e.g. using illumination controller 102D and light input ports 114), and detected by at least one light output element 116. The cross correlation, $CCA(\tau,\lambda)$, of the detected light intensity (I) at each wavelength $\lambda$ with signals $S_0$ at delay $\tau$ (constituting the data indicative of the detected light including ultrasound tagged light signals) has contributions from the ultrasound pressure amplitude as a function of delay $\tau$, $PA(\tau)$, and from the light distribution $LD(\lambda)$ in the monitored medium at depth z, where z is a function of $\tau$ as will be shown below. In other words, $CCA(\tau,\lambda)$ represents the light distribution at wavelength $\lambda$ at depth z multiplied by the acoustic power distribution or pressure amplitude, or a function of the acoustic pressure amplitude ($PA(\tau)$) at a distance z from the acoustic transducer.

Figure 2:
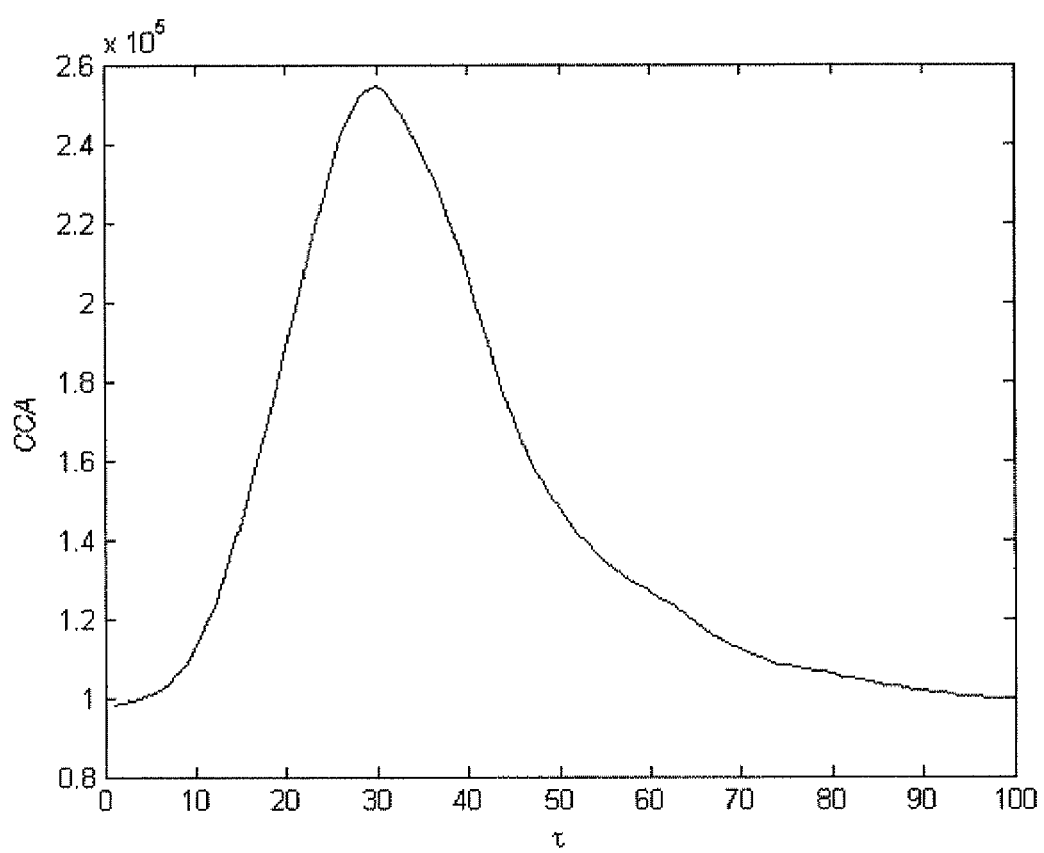
FIG. 2 shows an example of a CCA($\lambda$,$\tau$) signal as a function of delay time $\tau$.

As indicated above, the time parameter $\tau$ is the time delay within a single $CCA(\lambda,\tau)$ signal from the onset of the signal generated by acoustic generator. FIG. 2 shows an example of a $CCA(\lambda,\tau)$ signal as a function of delay time $\tau$; this graph is actually indicative of the signal dependence on the z-coordinate in the medium where the signal has been generated (where the "tagging" occurred). The time parameter $\tau$ signifies the depth coordinate (z) along the path of the acoustic signal within the monitored region according to the following:

$$z = \int_0^\tau v_{US}(\tau')d\tau',$$

where $v_{US}(\tau)$ is the ultrasound velocity within the region of the monitored medium reached by the ultrasound at a delay $\tau$.

Figure 3:
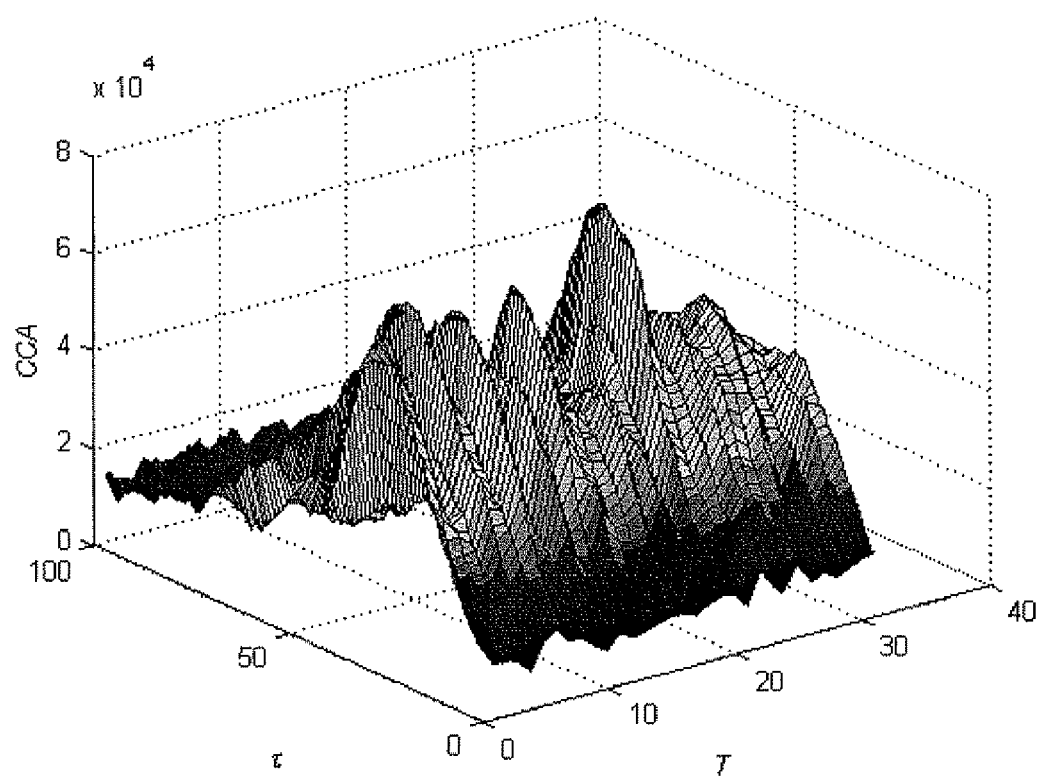
FIG. 3 exemplifies the CCA(T, $\lambda$, $\tau$) for different time stamps T.

Each $CCA(\lambda,\tau)$ signal carries its own time stamp T which signifies the time of the onset of the acoustic signal. An example of such signals, calculated for different times T and different time delays $\tau$ is shown in FIG. 3 and is therefore marked $CCA(\lambda, \tau, T)$.

Figure 4:
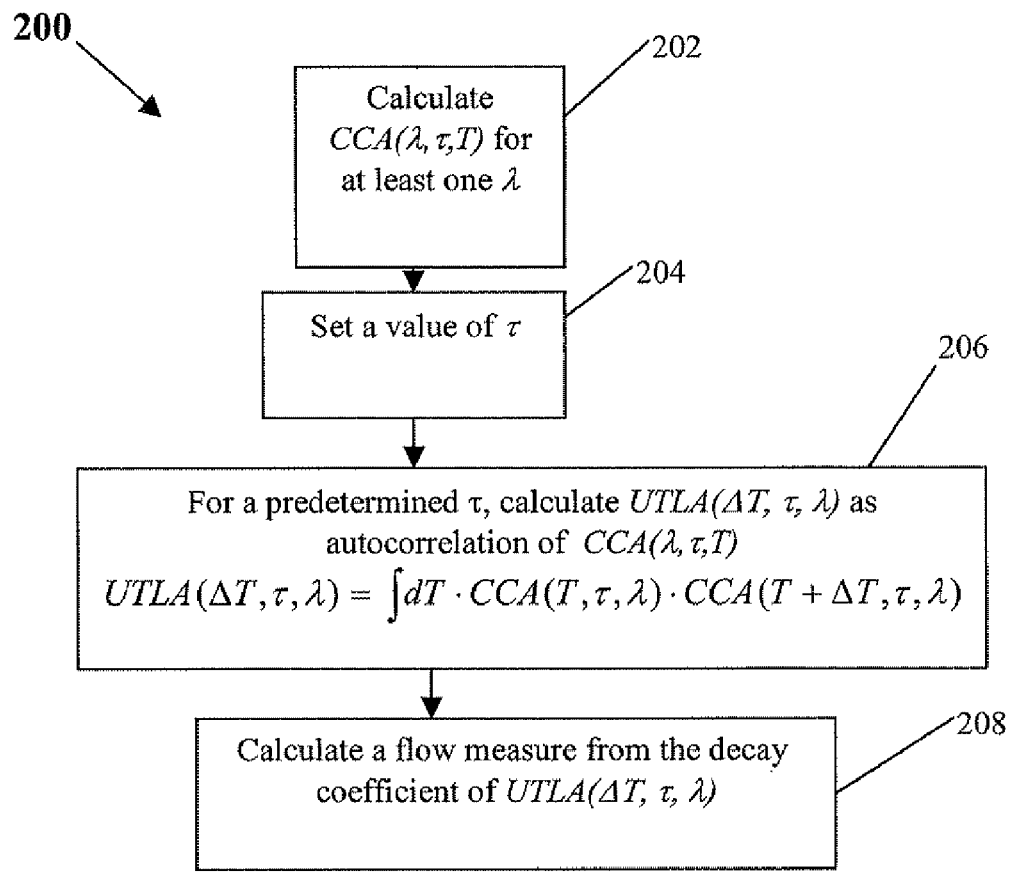
FIG. 4 shows a flow diagram of a method of the invention for calculating a flow parameter from the autocorrelation of CCA($\lambda$,$\tau$)

Referring to FIG. 4, there is exemplified a flow diagram 200 of a method of the invention for calculation of function UTLA, being the autocorrelation of the $CCA(\tau, \lambda, T)$ at different times T. More specifically, $CCA(\lambda, \tau, T)$ for at least one wavelength $\lambda$ is calculated by the correlator module of the processing utility (step 202), and a certain value of $\tau$ is set (step 204). For a predetermined $\tau$, $UTLA(\Delta T, \tau, \lambda)$ is calculated as autocorrelation of $CCA(\lambda,\tau,T)$ as follows (step 206):

$$UTLA(\Delta T,\tau,\lambda)=\int dT \cdot CCA(T,\tau,\lambda) \cdot CCA(T+\Delta T,\tau,\lambda) \quad (1)$$

Then, a flow measure can be calculated from the decay coefficient of $UTLA(\Delta T, \tau, \lambda)$—step 208. This is associated with the following:

UTLA decays with increasing $\Delta T$, the decay being characterized by a decay constant $T_{decay}$, which depends on the tissue properties. For example, the decay can be exponential:

$$UTLA(\Delta T,\tau,\lambda) \propto \exp(-\Delta T/T_{decay}). \quad (2)$$

The CCA signal and thus the UTLA signal are affected by the movement of scattering centers within the monitored medium. Variations in the distribution of scattering centers lead to a decorrelation of the UTLA signal. Thus, $T_{decay}$ is indicative of variations and rate of variations in the scattering centers' distribution within the monitored medium. More specifically, a flow within the monitored medium leads to a variation of the scattering centers within the medium and therefore to changes in the decay constant $T_{decay}$. An increase in flow within the monitored medium leads to a shorter correlation time between CCA signals, and a smaller $T_{decay}$, while a decrease in flow leads to a larger $T_{decay}$.

UTLA is a function of $\tau$, and therefore a function of the depth coordinate z along the ultrasound path into the monitored medium. Hence, UTLA provides information indicative of a measure of flow within the medium as a function of depth.

In the above-described example, generation of an acoustic wave by a coded signal with narrow autocorrelation was considered. The invention is not limited to this specific example.

In some other embodiments of the invention, the acoustic radiation is generated by signal $S_0$ in the form of a pulse or a series of pulses ($PU(T)$), i.e., not necessarily a coded signal. Light of wavelength $\lambda$ is irradiated into the medium, and detected by at least one light output element. The cross correlation $CCA(\tau,\lambda)$ is that of the detected light intensity at wavelength $\lambda$ with the pulse or series of pulses that generate the acoustic signal, the time parameter $\tau$ being the time within a single CCA signal. Each CCA signal carries its own time stamp T which signifies the time the acoustic signal was generated. Using short pulses allows for probing variations on shorter time scales.

The UTLA signal, being an autocorrelation of the $CCA(\tau, \lambda)$ at different times T, is calculated according to equation (1) above, and the decay time $T_{decay}$ is measured, thus providing information indicative of a measure of flow within the monitored medium. Depending on the time resolution requirement, $T_{decay}$ can be calculated from a single UTLA signal or from a sum/average over such signals.

In yet other embodiments of the invention, the generated acoustic signal is a continuous wave (CW), or a series of phase synchronized pulses (i.e. modulated CW). Light of wavelength $\lambda$ is irradiated into the medium, and detected by at least one light output element. The spectral width of the power spectrum of the detected light intensity ($|I(\Omega)|^2$) is peaked around at least two frequencies: 0 Hz (i.e. DC) and at the ultrasound frequency ($F_0$) and its harmonics (multiples of $F_0$). A measure of flow in the monitored medium is defined according to parameters of at least the peak at $F_0$. Furthermore, a measure of flow in the monitored medium can be characterized by a combination of parameters from the peak at $F_0$ and/or the peaks at its harmonics, and/or the DC peak.

Figure 5:
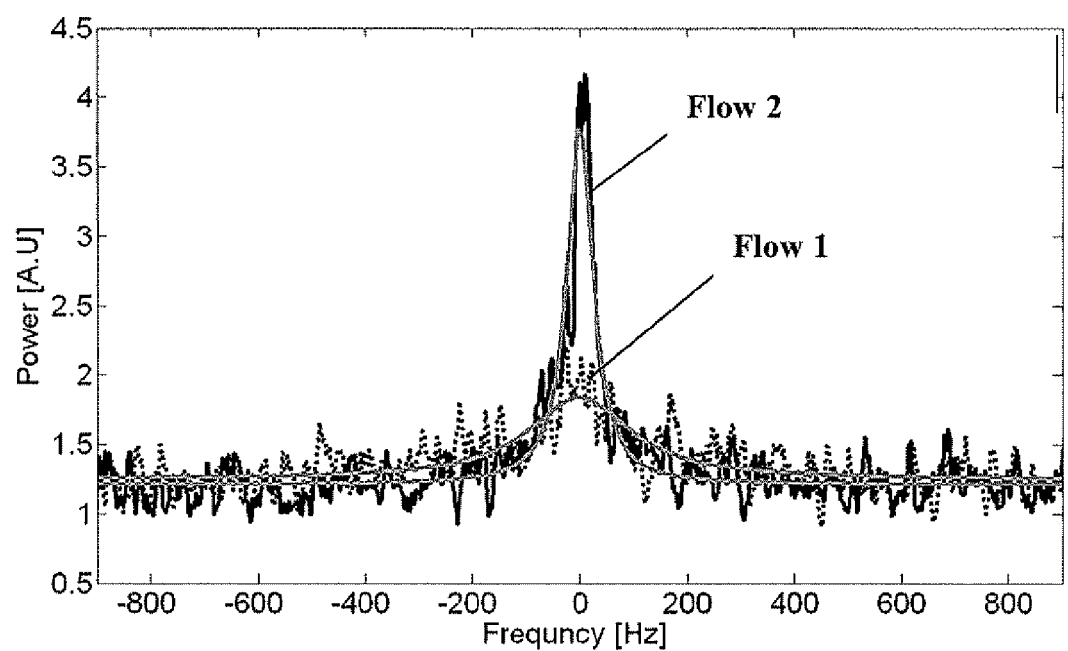
FIG. 5 shows the light intensity power spectrum in the vicinity of the ultrasound frequency (marked as "0")

An example for the power spectrum around $F_0$ is shown in FIG. 5. In this example a CW ultrasound wave of $F_0$=1 MHz was transmitted into the tissue by an ultrasound transducer (acoustic output 112) positioned between two optical fibers (light input 114 and light output 112). The signal output of the photodetector was digitized and the power spectrum of the collected light was calculated for two flow conditions, Flow 1 and Flow 2 where Flow1>Flow2. As can be seen, the width of the power spectrum during Flow 1 is wider than that during Flow 2 and its peak is lower.

The width of the power spectrum peaks is affected by frequency broadening effects, such as Doppler broadening due to Brownian motion of scattering centers within the monitored medium. When there is an increase in flow, the spectral width increases, while a decrease in flow results in a narrower power spectrum. The power spectrum width is therefore indicative of a measure of flow.

For example, the spectral width can be determined as the width of a Lorentzian fit to the power spectrum. As another example, one can measure the full width at half maximum amplitude of the power spectrum at $F_0$. Other methods can be used to correlate a parameter of the power spectrum (e.g. width, standard deviation, peak amplitude, or any other fitting function) to the flow in the underlying monitored medium. In addition, comparisons to matching parameter measures for the DC power spectrum can be made. These can contribute to an increase in the measurement accuracy, reduce error and improve stability of the measurement.

Figure 6:
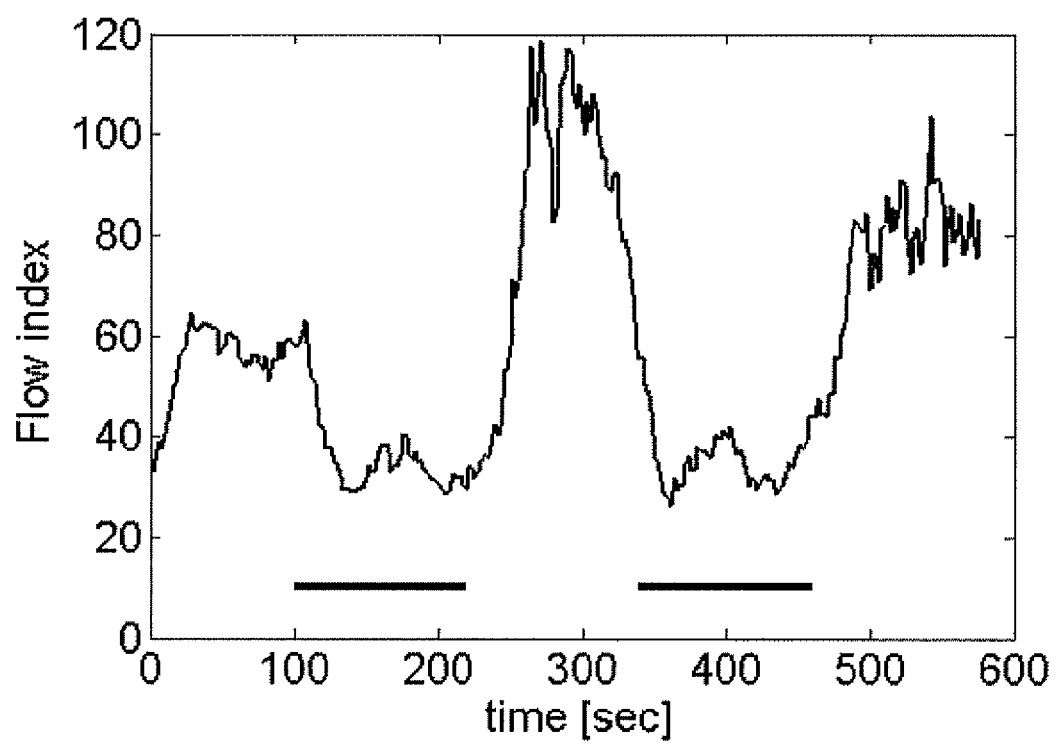
FIG. 6 shows a flow index defined according to the width of the power spectrum, as a function of time, during a measurement on a human arm that includes two cuff occlusions marked by two straight bold lines.

An example of a measurement of flow during a cuff occlusion performed on a human arm is shown in FIG. 6. The cuff is inflated two times, with a reflow in between the two inflations. A flow index was defined according to spectral width (i.e. the width of the distribution according to a Lorentzian shape was correlated to the flow, and is defined as the flow index). The flow index is plotted as a function of time. As clearly seen in the figure, during the cuff occlusions (marked by dark bold straight lines below the curve), the flow index decreased significantly, while an expected increase in flow due to hyperemia can clearly be seen between the cuffing episodes. A calibration curve can thus be calculated, based on simultaneous measurement of different flow conditions (for example, different flow velocities, or different volume/min) to provide a scaled measurement of flow.

Figure 7:
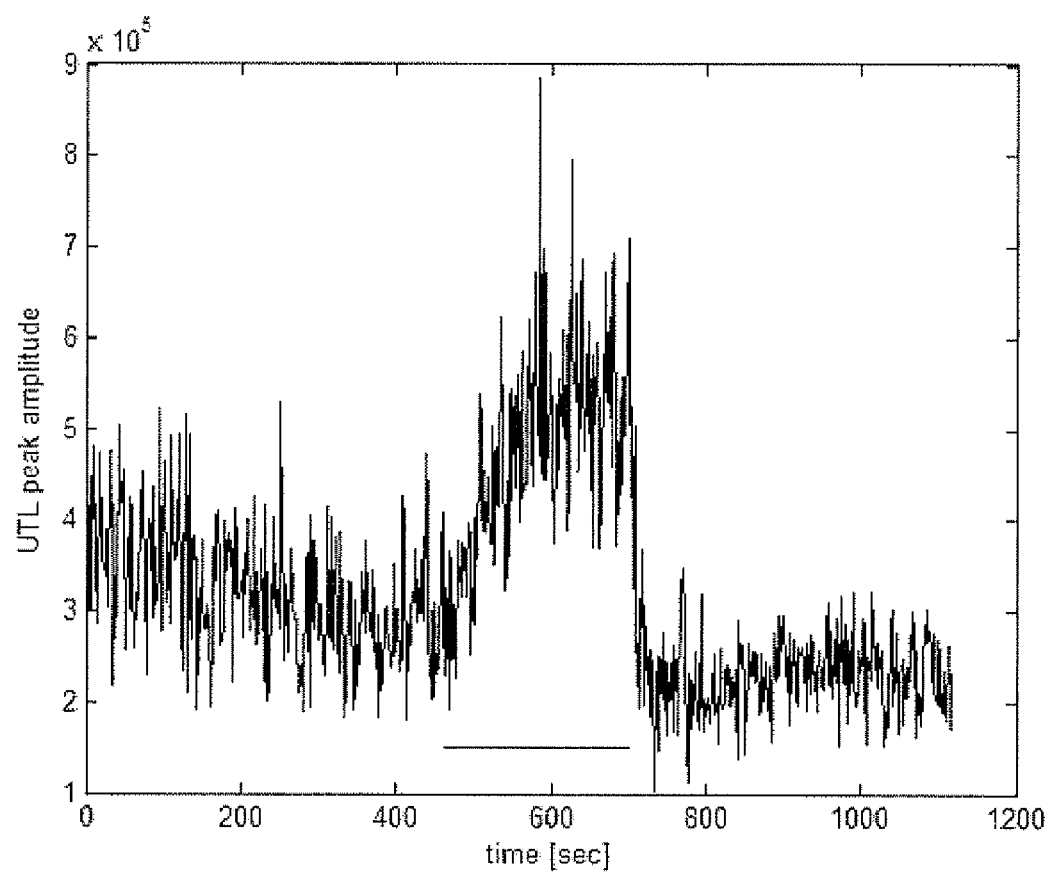
FIG. 7 illustrates influence of flow on the amplitude of the CCA($\lambda$,$\tau$) signal during a session of cuff occlusion when the light and ultrasound are emitted into the patient's arm.

Turning back to FIG. 2, the amplitude of the $CCA(\lambda,\tau)$ signal at a predetermined delay time $\tau$ is affected by flow in the underlying monitored medium. An increase in flow results in a decrease in the $CCA(\lambda,\tau)$ signal amplitude, while a decrease in flow results in an increase in the $CCA(\lambda,\tau)$ signal amplitude. In particular, flow in the underlying monitored medium affects the peak $CCA(\lambda,\tau)$ amplitude. Such an example is shown in FIG. 7, depicting the influence of blood flow in a patient's arm on the peak amplitude of the $CCA(\lambda,\tau)$ signal during a session of cuff occlusion when the light and ultrasound were emitted into the patient's arm. The flow index was taken to be a function of the inverse $CCA(\lambda,\tau)$ peak height. During the cuff occlusion, the blood flow decreased.

Those skilled in the art will appreciate that various modifications and changes can be applied to the embodiments of the invention described hereinabove without departing from its scope defined in and by the appended claims.

The invention claimed is:

1. A monitoring system for monitoring fluid flow in turbid medium, the system comprising: a processor utility which is connectable to an acoustic generator associated with one or more acoustic ports and is operable for generating signals $S_0$ to activate said one or more acoustic ports for generating acoustic radiation of a certain frequency range centered at a frequency $F_0$ to irradiate a region of interest and is connectable to at least one light output port associated with one or more light detectors for receiving light of at least one wavelength $\lambda$ from the region of interest including light tagged by said acoustic radiation, the processor utility being configured and operable for analyzing the signals $S_0$ and data indicative of the received light including light tagged by the corresponding acoustic radiation and determining correlation between said signals $S_0$ and said data indicative of the received light, said correlation being informative of a measure of fluid flow in the medium.

2. A monitoring system according to claim 1, wherein the acoustic radiation has one of the following profiles: a continuous wave (CW); a modulated continuous wave; and a pulse or sequence of pulses.

3. A monitoring system according to claim 1, wherein the processor utility is configured and operable to determine said correlation by carrying out the following:
   determining cross correlation, $CCA(\tau, \lambda, T)$, between said signal $S_0$ generated by acoustic generator and said data indicative of the received light, said cross correlation being calculated for each wavelength $\lambda$ of light and at a time delay $\tau$ from onset of signal S, and
   determining auto correlation UTLA of said cross correlation $CCA(\tau, \lambda, T)$ at different times T being time stamps of different measurement times, said autocorrelation UTLA being indicative of a measure of fluid flow within the medium as a function of depth z in the medium.

4. A monitoring system according to claim 3, wherein the processor utility is configured for determination of said autocorrelation UTLA for a predetermined $\tau$, being a function of $\Delta T$, $\tau$ and $\lambda$, as follows:

$$UTLA(\Delta T,\tau,\lambda)=\int dT \cdot CCA(T,\tau,\lambda) \cdot CCA(T+\Delta T,\tau,\lambda),$$

and determining the flow measure from a decay coefficient of UTLA ($\Delta T, \tau, \lambda$).

5. A monitoring system according to claim 4, wherein the acoustic signal is a coded signal with a narrow autocorrelation.

6. A monitoring system according to claim 4, wherein the processor utility is configured for measuring a decay time $T_{decay}$, thus providing information indicative of the measure of flow within the monitored medium.

7. A monitoring system according to claim 6, wherein the processor utility is configured for calculating the decay time $T_{decay}$ from a single UTLA signal or from a sum/average over such signals.

8. A monitoring system according to claim 6, wherein the acoustic signal is in the form of a pulse or a series of pulses.

9. A monitoring system according to claim 7, wherein the acoustic signal is in the form of a pulse or a series of pulses.

10. A monitoring system according to claim 1, comprising a control panel associated with a measurement unit, said control panel comprising at least one light input for illumination of the region of interest with light of one or more wavelengths, said at least one light output, and said one or more acoustic ports.

11. A monitoring system according to claim 10, wherein the at least one light input is associated with one or more light sources producing light of different wavelengths, or at least one tunable light source.

12. A monitoring system for monitoring fluid flow in a turbid medium, the system comprising: a processor utility which is connectable to an acoustic generator associated with one or more acoustic ports and is operable for generating signals $S_0$ to activate said one or more acoustic ports for irradiating a region of interest with acoustic radiation of a certain frequency range centered at a frequency $F_0$ and is connectable to at least one light output port associated with one or more light detectors for receiving light of at least one wavelength $\lambda$ from the region of interest including light tagged by said acoustic radiation, the processor utility being configured and operable for analyzing data indicative of the received light including light tagged by the acoustic radiation; identifying in said data at least one of the following light intensity peaks: a peak around said frequency $F_0$, a peak around a harmonic of said frequency $F_0$; and determining a measure of the fluid flow according to parameters of said at least one peak.

13. A monitoring system according to claim 12, wherein said processor utility is further configured and operable for analyzing said data indicative of the received light including light tagged by the acoustic radiation; identifying in said data a DC intensity peak and using parameters of the at least two peaks for the fluid flow measure.

14. A monitoring system according to claim 12, wherein the acoustic signal is in the form of a continuous wave or a modulated continuous wave or pulses or a series pulses.

15. A monitoring system according to claim 13, wherein the acoustic signal is in the form of a continuous wave or a modulated continuous wave or pulses or a series pulses.

16. A monitoring system according to claim 12, comprising a control panel associated with a measurement unit, said control panel comprising at least one light input for illumination of the region of interest with light of one or more wavelengths, said at least one light output, and said one or more acoustic ports.

17. A monitoring system according to claim 13, comprising a control panel associated with a measurement unit, said control panel comprising at least one light input for illumination of the region of interest with light of one or more wavelengths, said at least one light output, and said one or more acoustic ports.

18. A monitoring system according to claim 14, comprising a control panel associated with a measurement unit, said control panel comprising at least one light input for illumination of the region of interest with light of one or more wavelengths, said at least one light output, and said one or more acoustic ports.

19. A monitoring system according to claim 16, wherein the at least one light input is associated with one or more light sources producing light of different wavelengths, or at least one tunable light source.

20. A monitoring system according to claim 17, wherein the at least one light input is associated with one or more light sources producing light of different wavelengths, or at least one tunable light source.

21. A monitoring system according to claim 18, wherein the at least one light input is associated with one or more light sources producing light of different wavelengths, or at least one tunable light source.

22. A monitoring system for monitoring a fluid flow in a turbid medium of a subject, the monitoring system comprising:
   at least one light input port associated with one more light sources for generating light of at least one wavelength $\lambda$ to illuminate a region of interest in the subject;
   an acoustic generator associated with at least one acoustic port, the acoustic generator being operable for generating signals $S_0$ to activate said at least one acoustic port for irradiating a region of interest with acoustic radiation of a certain frequency range centered at a frequency $F_0$;
   at least one light output port associated with one or more light detectors for receiving light of at least one wavelength $\lambda$ from the region of interest including light tagged by said acoustic radiation and generating data indicative thereof; and
   a processor utility which is connected to the acoustic generator and to the at least one light output port for receiving data indicative of the generated signals $S_0$ and said data indicative of the received light, the processor utility being configured and operable for carrying out at least one of the following:
   (i) analyzing said data indicative of the generated signals $S_0$ and said data indicative of the received light for determining correlation between them, and generating output data informative of a measure of the fluid flow in the region of interest in the subject; and
   (ii) analyzing said data indicative of the received light including light tagged by the acoustic radiation; determining data indicative of a power spectrum of the received light; identifying in said power spectrum at least one of the following light intensity peaks: a peak around said frequency $F_0$, a peak around a harmonic of said frequency $F_0$; and determining a measure of the fluid flow according to parameters of said at least one peak.

23. A control unit for use in monitoring fluid flow in a turbid medium, the control unit comprising a processor utility configured for communication with an acoustic generator for receiving data indicative of signals $S_0$ corresponding to signals which activate one or more acoustic ports for irradiating a region of interest with acoustic radiation of a certain frequency range centered at a frequency $F_0$ and for communication with and one or more light detectors for receiving data indicative of detected light of at least one wavelength $\lambda$ including light tagged by said acoustic radiation, the processor utility being configured for processing and analyzing said data indicative of the detected light and generating output data indicative of correlation between said signals $S_0$ and said data indicative of the detected light, said correlation being informative of a measure of the fluid flow in the medium.

* * * * *